United States Patent
Häussler et al.

(10) Patent No.: US 6,871,572 B1
(45) Date of Patent: Mar. 29, 2005

(54) DRIVE FOR PRECISION OSCILLATIONS

(75) Inventors: Bernhard Häussler, Waghäusel (DE);
Rolf Rödel, Waghäusel (DE); Josef Pauli, Eppelheim (DE)

(73) Assignee: Max-Planck-Gesellschaft zur Forderung der Wissenschaften (DE)

( * ) Notice: Subject to any disclaimer, the term of this patent is extended or adjusted under 35 U.S.C. 154(b) by 39 days.

(21) Appl. No.: 10/111,505

(22) PCT Filed: Oct. 23, 2000

(86) PCT No.: PCT/EP00/10433
§ 371 (c)(1),
(2), (4) Date: May 29, 2002

(87) PCT Pub. No.: WO01/31314
PCT Pub. Date: May 3, 2001

(30) Foreign Application Priority Data

Oct. 25, 1999 (DE) .......................... 199 51 288

(51) Int. Cl.⁷ .............................. G01N 1/06; B26D 5/08
(52) U.S. Cl. .............................. 83/542; 83/597; 83/701; 83/915.5; 331/156; 331/177 R; 606/169; 310/317; 310/345
(58) Field of Search ............................... 83/523, 915.5, 83/597, 701, 956, 542; 74/469, 128, 155, 99 R, 471 R, 110, 133; 606/167, 169, 171, 178; 331/74, 155, 156, 177 R; 318/9, 119; 335/147, 209, 221, 223, 302; 324/415, 200, 158.1; 310/311, 316.01, 37, 345, 36, 323.01, 323.06, 323.21, 328; 359/391, 368, 393, 896; 73/1.81, 1.82, 579, 649, 662

(56) References Cited

U.S. PATENT DOCUMENTS 3,009,628 A * 11/1961 Kolfertz .................. 417/410.1
3,462,939 A * 8/1969 Tanaka et al. .............. 368/157
3,585,424 A * 6/1971 Neel ............................ 310/25
3,756,105 A * 9/1973 Balamuth et al. .............. 83/14
4,126,069 A   11/1978 Shimonaka
5,159,268 A * 10/1992 Wu .......................... 324/207.2
6,041,686 A   3/2000 Lihl et al.

FOREIGN PATENT DOCUMENTS

| AT | 181684 | 4/1955 |
| DE | 913 112 | 6/1954 |
| DE | 1 267 873 | 5/1968 |
| DE | 27 55 479 | 6/1978 |
| DE | 1561 99 | 8/1982 |
| DE | 93 00 297.1 | 5/1993 |
| DE | 196 45 107 | 5/1998 |
| DE | 156 199 | 2/2001 |
| EP | 57100335 | 6/1982 |
| EP | 0 216 579 | 4/1987 |
| EP | 0 924 503 | 6/1999 |
| JP | 07246367 | 9/1995 |
| JP | 11076939 | 3/1999 |
| JP | 2001347225 | * 12/2001 |

* cited by examiner

Primary Examiner—Boyer D. Ashley
(74) Attorney, Agent, or Firm—Piper Rudnick LLP

(57) ABSTRACT

A drive device for generating oscillations, especially for the blade of a microtome, with a power generator and a power transmission element, which with the power generator is movable in a predetermined oscillation direction (S), whereby the power generator includes a combination of a permanent magnet part and a coil part, whereof one part is fixed stationary on a holder and the other part on the power transmission element, respectively, and the power transmission element is formed by a vibrational arm, which is fixed at one end to the holder and which is elastically bendable in the oscillation direction and still in all other directions.

10 Claims, 3 Drawing Sheets

Slicer Type Campden "Jonas"
Frequency 30 Hz
Vertical movement: 24 µm

Slicer 2
Frequency: 30 Hz
Vertical movement: 4 µm

DRIVE FOR PRECISION OSCILLATIONS

FIELD OF THE INVENTION

The invention relates to a drive device for generating vibrations, in particular for precision tools and manipulators, such as for example a drive for the cutting tool of a microtome, and a microtome that is equipped with such a drive device.

BACKGROUND

Conventional microtomes for producing thin tissue sections are as a rule equipped with an eccentric drive, which sets a blade in a horizontal oscillation. By means of a feed device, the oscillating blade is passed through an object to be processed, fresh tissue for example, so that the desired section of the object is severed. The use of eccentric drives is bound up with a number of drawbacks. The oscillation frequency of the blade is limited, because with the eccentric drive the masses of a knife holder and guides also have to be accelerated. Furthermore, the oscillation amplitude of the blade is also restricted by the eccentric itself to around 1 mm as a rule. An essential drawback in the production of precision sections of biological materials is caused by the formation of vertical movements (vertical beats), which diverge from the horizontal oscillation direction of the blade. The eccentric drive generates a vertical beat at its reversal points. Furthermore, the tendency towards vertical oscillation increases at higher oscillation frequencies, at which the effective forces increase. As a result of the vertical oscillations, the tissue to be processed is separated not only in the feed direction. Cells in the tissue surface are also damaged. This makes the subsequent examination of the tissue section more difficult.

In a modified design of a microtome, such as is commercially available for example under the name "Vibracut 3", manufacturer: FTB Feinwerktechnik, the knife holder is caused to oscillate with a moving lift magnet. This form of drive is disadvantageous, since the vibration frequency of the blade is tied to the resonance frequency of the knife holder. Furthermore, it is in turn not possible to rule out vertical oscillations to the extent required for precision applications, especially in microbiology and neurology.

The stated problems with the vibrational drive of a microtome blade also arise with other precision tools and manipulators with which a linear oscillatory motion in a predetermined oscillation direction is desired, whilst in all other directions no deflection movements take place. This concerns, for example, tools for the processing of microsystems or micro-surgical instruments.

It would accordingly be advantageous to provide an improved drive device for generating vibrations, with which the drawbacks of the conventional drives for precision tools or manipulators are overcome and which in particular enables a generation of vibrations in a predetermined oscillation direction with an adjustable oscillation frequency and oscillation amplitude and without lateral deflections. It would also be advantageous to provide an improved microtome, with which the thickness of tissue sections can be reduced and the damage to tissue parts outside in the sectioning direction can be reduced.

SUMMARY OF THE INVENTION

According to a first aspect of the invention, a drive device (precision vibrational drive) in particular is created, which contains as a power generator a combination of a magnet with a permanent magnetic field and a magnet with a periodically variable magnetic field, with which a power transmission element can be set into an oscillatory motion relative to a stationary holder according to a predetermined oscillation direction. The power transmission element is formed in particular by a vibrational arm fitted on the holder, which vibrational arm comprises at least one plane-shaped strip of elastic material which is flexible in the oscillation direction and inflexible or stiffened in all other directions. The vibrational arm is preferably formed as a U-section. The open end of the U-section is fixed to the holder and the closed end of the U-section is elastically bendable in the section plane corresponding to the oscillation direction. According to a preferred embodiment of the invention, the magnet with the permanent magnetic field is a bell-shaped magnet and the magnet with the variable magnetic field is a plunger coil which is arranged in the bell-shaped magnet. The plunger coil is fixed at or near to the closed free end of the U-section of the power transmission element and is connected electrically to an oscillation generator.

According to a further aspect of the invention, the precision vibrational drive is driven in such a way that a forced oscillation is imparted to the power transmission element. The frequency and amplitude of the forced oscillation can be adjusted according to the desired motion characteristics of the tool or manipulator to be operated. According to a preferred embodiment, a control circuit is implemented for the frequency and amplitude adjustment using a bending sensor on the power transmission element.

According to a still further aspect of the invention, a microtome is described which is equipped with the aforementioned drive device. The power transmission element serves as a support of a microtome blade. The stationary holder of the power generator or the power transmission element is fitted on a precision feed in the form of a linear table.

The invention has the following advantages. The drive device according to the invention delivers an oscillatory motion in a fixed oscillation direction without lateral deflections, whereby the power transmission element is tied to the oscillation direction without mechanical guides solely by means of its shape, in particular its sectional shape. The oscillation frequency and amplitude are variable and adjustable independently of one another. The microtome according to the invention is distinguished by a greatly reduced vertical stroke. It is thus possible to produce tissue sections with minimum damage to the surface. The drive device according to the invention has an extended area of application also outside the microtome application.

BRIEF SUMMARY OF THE DRAWINGS

Further advantages and details of the invention will become apparent from the description of the appended drawings.

They show.

DETAILED DESCRIPTION

The invention is described in the following by reference to a drive device for a microtome with given oscillation parameters of the blade. The invention, however, is restricted neither to the microtome application nor to the oscillation parameters given by way of example.

Figure 1:
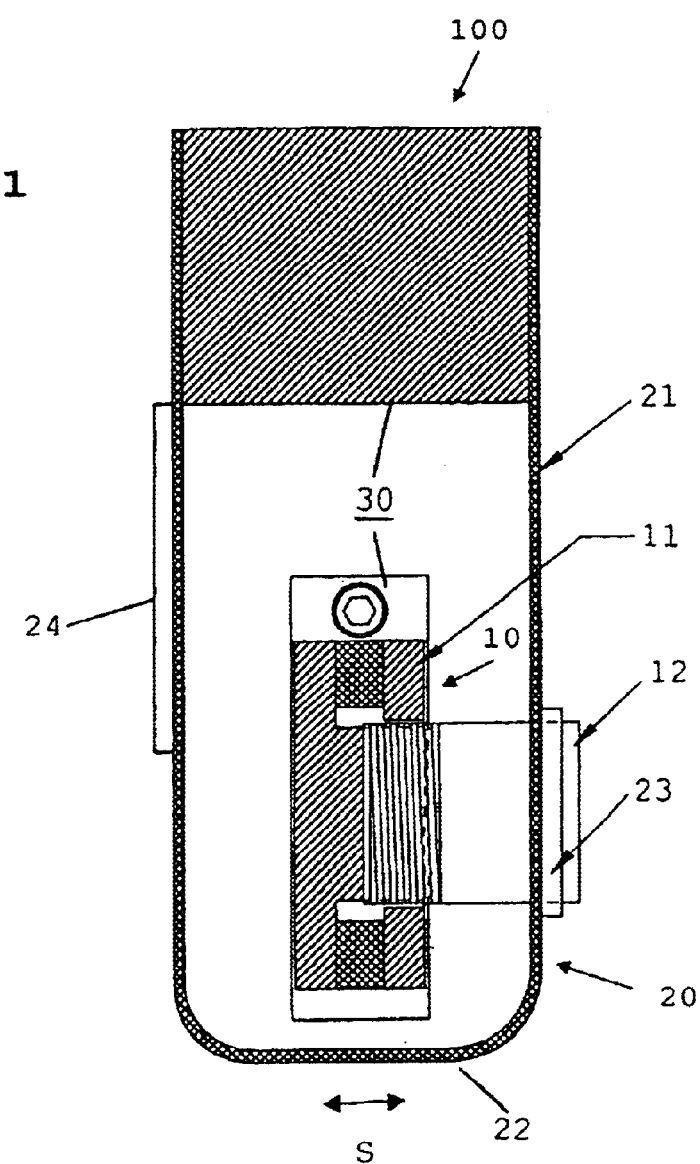
FIG. 1: a sectional view of an embodiment of the drive device according to the invention, FIGS. 2a & b: details of the power generator of the drive device according to FIG. 1, FIG. 3: an outline diagram of a microtome according to the invention, and FIGS. 4a & b: graphical representations to characterize the oscillatory motion of a blade of a microtome according to the invention.

Drive device 100 according to the invention comprises, according to the diagrammatic sectional view in FIG. 1, a power generator 10 and a power transmission element 20, which is movable in a predetermined oscillation direction (arrow S). The power generator comprises a permanent magnet part and a coil part. The permanent magnet part is formed by the bell-shaped magnet fitted stationary on a holder 30, the details of which bell-shaped magnet are explained by reference to FIGS. 2*a* & *b*. The coil part is a plunger coil 12, which projects into bell-shaped magnet 11. Plunger coil 12 is fixed to power transmission element 20.

Power transmission element 20 is formed by a vibrational arm 21, which is fixed at one end to holder 30 and is freely mobile at opposite end 22. Vibrational arm 21 is a U-profiled strip of a flat elastic material. This adjusts the mobility of free end 22 to bending in oscillation direction S. In all other directions diverging from oscillation direction S (in the drawing plane), vibrational arm 21 is a rigid structure immobile relative to holder 30. At free end 22 or close to the latter, plunger coil 12 is fixed with a fixing flange 23 to vibrational arm 21. Bell-shaped magnet 11 in the U-section and plunger coil 12 are position such that they are movable relative to one another in oscillation direction S. Generally, power transmission element 20 is designed as a support for a tool to be moved periodically or a manipulator or a tool holder. For this purpose, it has holding elements (not shown) on free end 22, depending on the application.

For use in a microtome, the drive device according to the invention essentially has dimensions shown in FIG. 1 (scale 1:1). The vibrational arm is made for example of aluminum sheet with a width of around 40 mm and a thickness of around 1 to 2 mm. The length of the vibrational arm is selected according to the application. With a length of around 10 cm, the natural frequency of represented vibrational arm 21 with a U-section amounts to around 80 Hz. If, depending on the application, larger or smaller frequency ranges (e.g. at around 10 Hz) are required, the vibrational arm should be designed accordingly with a smaller or greater length.

The parts of the drive device can be modified according to different embodiments. In the case of the power generator, it is possible to fix the coil part stationary on the holder and the permanent magnet part on the power transmission element. Furthermore, it is possible to use, as a permanent magnet part, a differently formed permanent magnet or also a coil which is driven with a constant excitation current. Finally, a piezo drive could also be used alternatively as a power generator. The power transmission element may also be formed by a single strip-shaped sheet (see FIG. 2*b,* which is flexible only at right angles to the sheet plane and otherwise rigid, or a complex profiled structure with only one flexural degree of freedom.

Reference numeral 24 relates to a piezo bending element, which if need be is fitted as a sensor on vibrational arm 21. The current oscillation amplitude of vibrational arm 21 can be detected with piezo bending element 24.

Figure 2A:
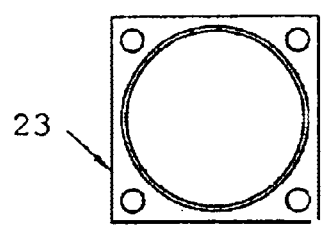
Figure 2A:
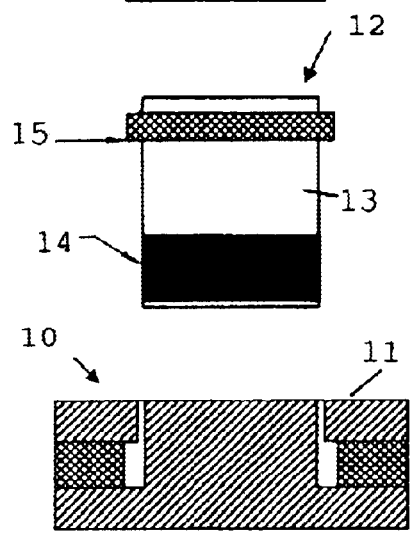
Figure 2B:
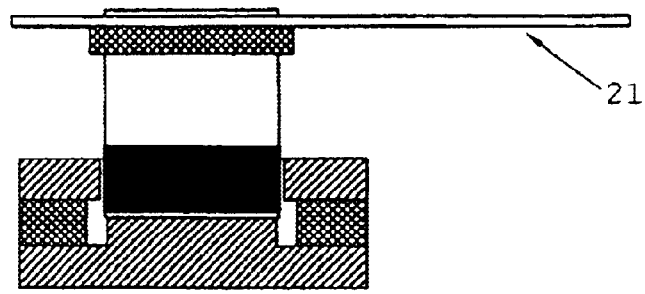

FIG. 2 shows details of power generator 10 in the disassembled (FIG. 2*a*) and assembled (FIG. 2*b*) state. Bell-shaped magnet 11 is made of highly permanent material (e.g. of neodymium, B=1.17 T). The structure of the bell-shaped magnet preferably corresponds to the structure of a bell-shaped magnet known per se, such as is used in loud speakers. Plunger coil 12 comprises a coil holder 13, coil winding 14 and a coil flange 15. Fixing flane 23, to which plunger coil 12 is fixed (e.g. glued) with coil flange 15, is fitted to vibrational arm 21 of the power transmission element.

Plunger coil 12 is connected electrically to a supply device. This contains an adjustable oscillation generator and a power amplifier (power e.g. 25 W). The oscillation generator is designed to generate electrical oscillations in a frequency range from 30 to 130 Hz. Through the power of the power amplifier, the oscillation amplitude of vibrational arm 21 can be adjusted continuously in the range from 0 to 1.5 mm. A particular advantage of the invention consists in the adjustment of forced oscillations of the power transmission element. In the presence of excitation at a frequency, selected according to application, which is different from the natural frequency of the power transmission element (with the respective tool or manipulator), its oscillation frequency and amplitude can be freely adjusted.

According to a preferred embodiment of the invention, a control circuit is arranged for the adjustment of the oscillation amplitude and/or frequency. The piezo bending element 24 on vibrational arm 21 is used as a sensor. Piezo bending element 24 is connected electrically to the supply device. Depending on the current oscillation amplitude of vibrational arm 21, the parameters of the supply device are changed for the adjustment of a certain target value.

Figure 3:
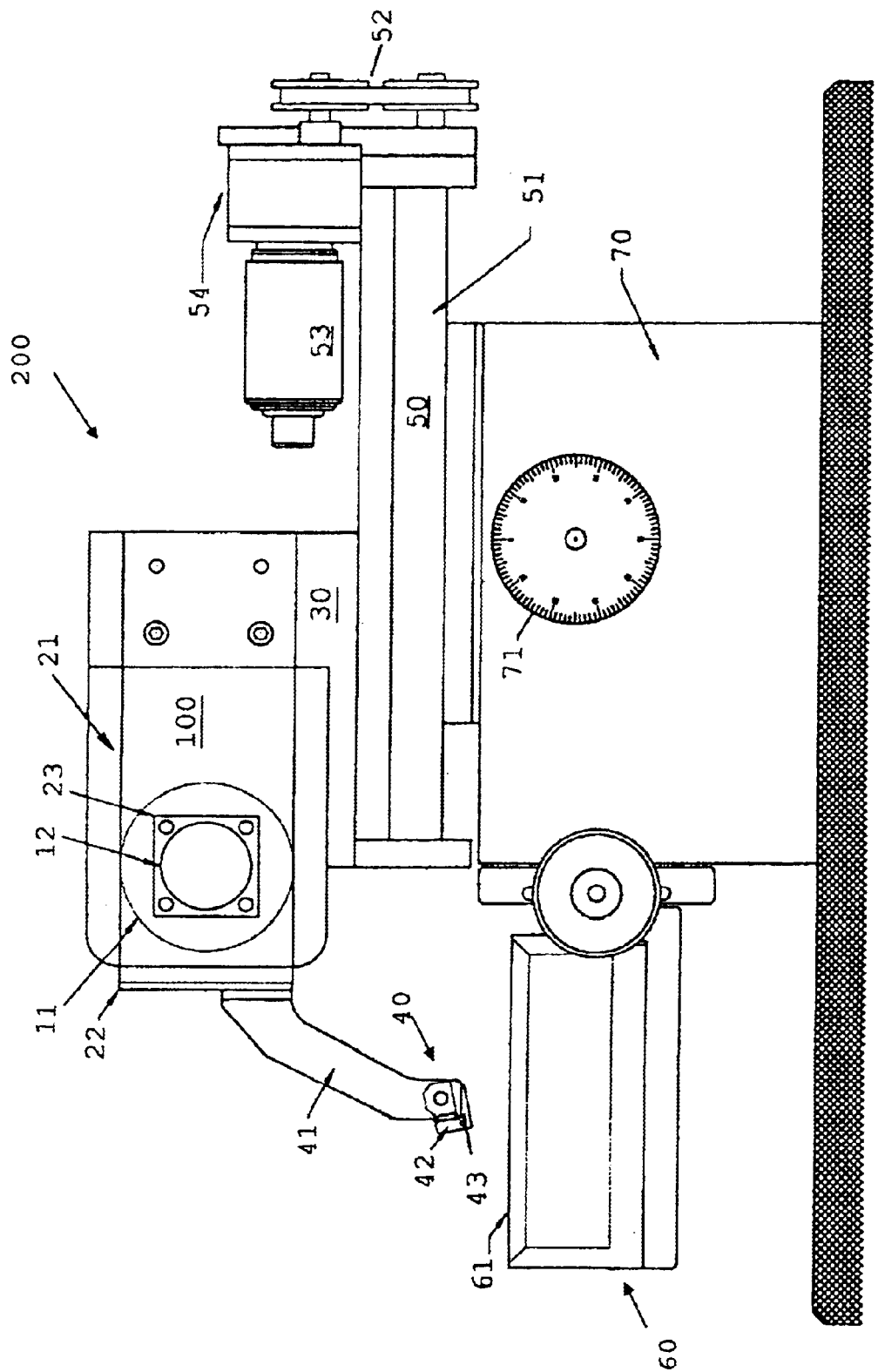

FIG. 3 illustrates in a diagrammatic side view a microtome 200 according to the invention, which is equipped with drive device 100 described above. Drive device 100 is constructed in accordance with the embodiment illustrated in FIGS. 1 and 2. In particular, vibrational arm 21 with fixing flange 23, plunger coil 12, permanent magnet 11 (dashed) and holder 30 are illustrated in FIG. 3. A tool 40 is fixed to free end 22 of vibrational arm 21. Tool 40 comprises a vibrating fork 41, which forms an extension arm for the blade. Knife holder 42 with blade 43 is fitted at the end of the extension arm. Knife holder 42 is fitted in a swivelling manner relative to vibrating fork 41. With drive device 100, horizontally aligned blade 43 is mobile in an oscillating manner in the oscillation direction at right angles to the drawing plane.

Furthermore, microtome 200 comprises a feed device 50 and a dissecting area 60, which are accommodated on a lifting table 70. Feed device 50 includes a linear table 51 known per se, which is driven by a spindle, gearing 52 and a d.c. motor 53. The d.c. motor is equipped with a d.c. tacho unit 54. A speed control is not required due to the provision of a large gear reduction of around 200:1. The d.c. tacho unit generates a direct voltage which is proportional to the rate of feed and is displayed for example by a digital voltameter.

Dissection area 60 comprises a dissection tank 61, in which the object to be processed, a biological tissue for example, is accommodated. In place of tank 61, any other form of specimen holder may also be provided (e.g. a platform or a clamping support). With an adjustment device 71 on lifting table 70, the height of blade 43 is adjusted relative to dissection tank 61. For a rough adjustment, dissection area 60 may also be displaceable relative to lifting table 70. Adjustment device 71 is, for example, a micrometer screw. A graduation mark corresponds to 1 μm in the example shown.

To use microtome 200, a specimen is positioned in dissection tank 61. Blade 43 is returned to a starting point by feed device 50. The desired height of the blade is then adjusted with adjustment device 71. Drive device 100 is actuated, so that blade 43 performs horizontal oscillations. Simultaneously, oscillating blade 43 is driven by feed device 50 through the specimen, so that a section of the specimen is lifted off and lies on blade 43.

Any suitable cutting tool, for example a razor blade, can be used as blade 43. To make optimum use of the oscillation capacity of the drive device according to the invention, which is essentially free from vertical strokes, a blade made of an inflexible material, for example a ceramic knife, is however preferred.

Figure 4A:
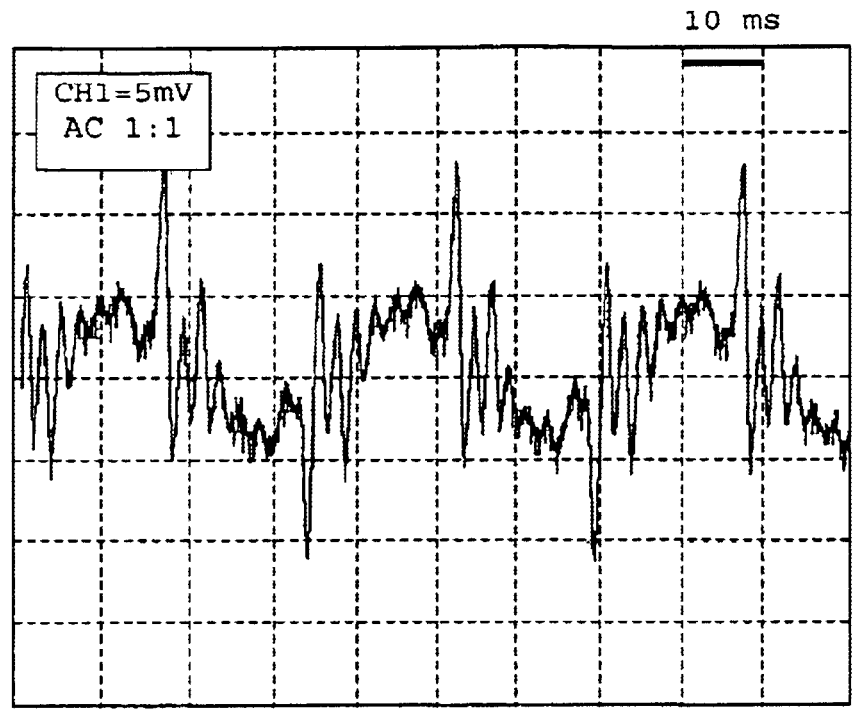
Figure 4B:
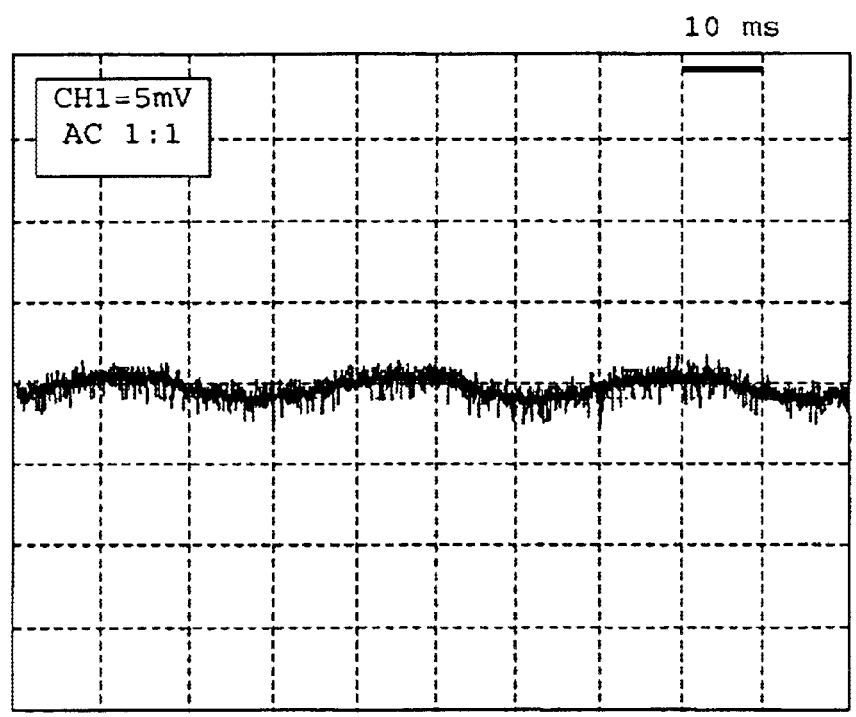

An important advantage of the invention, i.e. the considerable reduction in the vertical beat of the blade, is illustrated in FIGS. 4a & b. With a contactless inductive path sensor (e.g. sensor system IS 115, firm Micro-Epsilon), the vertical vibrations of the blade of a conventional microtome (with eccentric drive, FIG. 4a) and a microtome according to the invention (FIG. 4b) are recorded as a function of time. The graphical representations show a vertical beat of around 24 μm for the conventional microtome. The vertical beat of the blade with the microtome according to the invention is 5 to 2 μm in the frequency range from 30 to 130 Hz with amplitude of 1 mm.

In alternative applications, the drive device according to the invention is used for the actuation of tools or manipulators for microsystem technology or of microsurgical tools or instruments. Several drive devices can also be combined with one another, in that the holder of a first drive device is itself caused to oscillate with another drive device in order to generate variable oscillation directions or periodic movements of the tool or manipulator along predetermined curved paths.

What is claimed is:

1. A vibrational device for a tool or a manipulator comprising:
    a power transmission element which forms a support for the tool or the manipulator,
    a power generator comprising a permanent magnet part and a coil part, wherein one of the parts is fixed on a holder and another of the parts is fixed on the power transmission element, and
    a bending sensor for detecting oscillation amplitude of the power transmission element on the power trnasmission element,
    wherein the power transmission element is movable by the power generator in a predetermined oscillation direction, and is formed from a vibrational arm which is formed from a strip of flat material shaped to have a U-shaped section and has an open end and a closed free end, the open end being fixed to the holder and the closed free end being elastically bendable in the oscillation direction and substantially rigid in other directions, and
    wherein one component of the permanent magnet part and the coil part is fixed to the holder while another component of the permanent magnet part and the coil part is fixed to the vibrational arm.

2. The drive device according to claim 1, wherein the permanent magnet part is a bell-shaped magnet fixed to the holder, and the coil part is a plunger coil fixed to the power transmission element.

3. The drive device according to claim 1, wherein the coil part is electrically connected to a supply device containing an oscillation generator for generating a predetermined output frequency for excitation of the coil part.

4. The drive device according to claim 2, wherein the oscillation generator is adapted to generate an output frequency different from the natural frequency of the power transmission element.

5. The drive device according to claim 1, wherein the tool is a cutting tool of a microtome.

6. The drive device according to claim 5, wherein the cutting tool is a ceramic knife.

7. A microtome equipped with a drive device according to claim 1.

8. The microtome according to claim 7, further comprising a control circuit for adjusting a predetermined oscillation amplitude and frequency of a cutting tool of the microtome which contains the bending sensor.

9. The microtome according to claim 7, further comprising a control circuit for adjusting a predetermined oscillation amplitude or frequency of the cutting tool which contains the bending sensor.

10. A process for generating oscillations with a vibrational device for a tool or a manipulator comprising a power transmission element which forms a support for the tool or the manipulator, and a power generator comprising a permanent magnet part and a coil part, wherein one of the parts is fixed on a holder and another of the parts is fixed on the power transmission element, wherein the power transmission element is movable by the power generator in a predetermined oscillation direction and is formed from a vibrational arm which is formed from a strip of flat material shaped to have a U-shaped section and has an open end and a closed free end, the open end being fixed to the holder and, the closed free end being elastically bendable in the oscillation direction and substantially rigid in other directions, and wherein one component of the permanent magnet part and the coil part is fixed to the holder while another component of the permanent magnet part and the coil part is fixed to the vibrational arm, comprising:
    applying to the coil part of the power generator an excitation frequency different from the natural frequency of the power transmission element, and
    exciting the coil part by adjusting electrical parameters determined in a control circuit with a bending sensor.

\* \* \* \* \*

UNITED STATES PATENT AND TRADEMARK OFFICE
CERTIFICATE OF CORRECTION

PATENT NO. : 6,871,572 B1
DATED : March 29, 2005
INVENTOR(S) : Haussler et al.

It is certified that error appears in the above-identified patent and that said Letters Patent is hereby corrected as shown below:

<u>Title page,</u>
Item [73], Assignees, please change "Max-Planck-Geselleschaft zur" to
-- Max-Planck-Gesellschaft zur --.

Signed and Sealed this

Twenty-first Day of June, 2005

JON W. DUDAS
*Director of the United States Patent and Trademark Office*